US010962550B2

(12) United States Patent
Goldman

(10) Patent No.: US 10,962,550 B2
(45) Date of Patent: *Mar. 30, 2021

(54) ANALYSIS OF AMINO ACIDS IN BODY FLUID BY LIQUID CHROMATOGRAPHY-MASS SPECTROMETRY

(71) Applicant: Quest Diagnostics Investment Incorporated, Wilmington, DE (US)

(72) Inventor: Scott Goldman, Laguna Niguel, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,291

(22) Filed: Jan. 7, 2019

(65) Prior Publication Data
US 2019/0145983 A1    May 16, 2019

Related U.S. Application Data

(63) Continuation of application No. 15/875,850, filed on Jan. 19, 2018, now Pat. No. 10,203,337, which is a continuation of application No. 12/646,666, filed on Dec. 23, 2009, now Pat. No. 8,969,089, which is a continuation-in-part of application No. PCT/US2008/068653, filed on Jun. 27, 2008.

(60) Provisional application No. 60/947,338, filed on Jun. 29, 2007.

(51) Int. Cl.
*G01N 33/68* (2006.01)
*H01J 49/00* (2006.01)

(52) U.S. Cl.
CPC ....... *G01N 33/6848* (2013.01); *G01N 33/689* (2013.01); *H01J 49/0031* (2013.01); *H01J 49/0036* (2013.01); *G01N 2333/4704* (2013.01); *G01N 2333/705* (2013.01); *G01N 2800/368* (2013.01); *H01J 49/004* (2013.01); *H01J 49/0045* (2013.01)

(58) Field of Classification Search
CPC ..... G01N 2333/4704; G01N 2333/705; G01N 2800/368; G01N 33/6848; G01N 33/689; H01J 49/0031; H01J 49/0036; H01J 49/004; H01J 49/0045; H01L 21/6831; H01L 21/6833; H02N 13/00; Y10T 279/23; Y10T 29/49124
See application file for complete search history.

(56) References Cited

U.S. PATENT DOCUMENTS

| 5,534,440 A | 7/1996 | Aebersold et al. |
| 5,559,038 A | 9/1996 | Kolhouse et al. |
| 5,885,841 A | 3/1999 | Higgs, Jr. et al. |
| 5,968,515 A | 10/1999 | Thacker |
| 6,692,971 B2 | 2/2004 | Shushan et al. |
| 6,977,143 B1 | 12/2005 | Caulfield et al. |
| 7,122,377 B2 | 10/2006 | Qiu et al. |
| 7,700,364 B2 * | 4/2010 | Goldman ............... G01N 30/06 436/89 |
| 8,945,933 B2 * | 2/2015 | Le ...................... G01N 33/6848 436/86 |
| 8,969,089 B2 * | 3/2015 | Goldman ............... G01N 30/06 436/89 |
| 10,175,208 B2 * | 1/2019 | Goldman ............... G01N 30/06 |
| 2003/0153007 A1 | 8/2003 | Chen et al. |
| 2003/0199102 A1 * | 10/2003 | Ostrup .................. B01L 3/5085 436/173 |
| 2006/0183238 A1 | 8/2006 | Nimkar et al. |
| 2007/0269899 A1 | 11/2007 | Shimbo et al. |

FOREIGN PATENT DOCUMENTS

| CN | 1825113 A | 8/2006 |
| EP | 1750126 A1 | 2/2007 |
| JP | S62209055 A | 9/1987 |
| JP | 2006003347 A | 1/2006 |
| JP | 2006513702 A | 4/2006 |
| JP | 2007024822 A | 2/2007 |
| JP | 2007163423 A | 6/2007 |
| JP | 2016047161 A | 4/2016 |
| WO | 03027681 A2 | 4/2003 |
| WO | 03069328 A1 | 8/2003 |
| WO | 2005116629 A1 | 12/2005 |
| WO | 2007003344 A2 | 1/2007 |

OTHER PUBLICATIONS

Parvy P., et al., "A New Pitfall in Plasma Amino Acid Analysis," Clinical Chemistry, 1989, vol. 35 (1), pp. 178.
Perwaiz S., et al., "Determination of Bile Acids in Biological Fluids by Liquid Chromatography-Electrospray Tandem Mass Spectrometry," Journal of Lipid Research, 2001, vol. 42 (1), pp. 114-119.
Phenomenex.com EZFaast Product Overview and Amino Acid Analysis, 2003. Retrieved from the Internet:, pp. 286-292, & product overview pp. 1-2.
Ruffin P., et al., "Column Chromatography of Cysteinesulfinic Acid, Cysteic Acid, and S-Sulfocysteine," Analytical Biochemistry, 1976, vol. 76 (I), pp. 233-238.
Schmid R., et al., "Effect of Somatostatin on Skin Lesions and Concentrations of Plasma Amino Acids in a Patient with Glucagonamoa-Syndrome," Hepatogastroenterology, 1988, vol. 35 (1), pp. 34-37.
Shiraishi S., et al., "Simultaneous Measurement of Serum Testosterone and Dihydrotestosterone by Liquid Chromatography-Tandem Mass Spectrometry," Clinical Chemistry, 2008, vol. 54 (11), pp. 1855-1863.

(Continued)

*Primary Examiner* — Marcela M Cordero Garcia
(74) *Attorney, Agent, or Firm* — Quest Diagnostics, Inc.

(57) ABSTRACT

This disclosure provides methods for quantifying individual amino acids in various bodily fluids obtained from a human patient. Also provided are reference ranges for normal amino acid levels in the various bodily fluids (e.g., blood plasma, urine, cerebrospinal fluid, and saliva) and for various age groups (e.g., neonates, infants, children, and adults).

6 Claims, 2 Drawing Sheets

(56) References Cited

OTHER PUBLICATIONS

Sido B., et al., "Impairment of Intestinal Glutathione Synthesis in Patients with Inflammatory Bowel Disease," Gut, 1998, vol. 42 (4), pp. 485-492.
Sigma-Adrich, Product Detail for C2196 013 L-Cystein S-sulfate [Online], 2009. Retrieved from the Internet:, http://www.sigmaaldrich.com/catalog/ProductDetail.do?D7=0&N5=SEARCH_Contact (2009). page 1 of 1.
Soga T., et al., "Amino Acid Analysis by Capillary Electrophoresis Electrospray Ionization Mass Spectroscopy," Analytical Chemistry, 2000, vol. 72 (6), pp. 1236-1241.
Staedt U., et al., "Effects of Ornithine Aspartate on Plasma Ammonia and Plasma Amino Acids in Patients with Cirrhosis. A Double-Blind, Randomized Study Using a Four-Fold Crossover Design," Journal of Hepatology, 1993, vol. 19 (3), pp. 424-430.
Stein W.H., et al., "The Amino Acid Content of the Blood and Urine in Wilson's Disease," Journal of Clinical Investigation, 1954, vol. 33 (3), pp. 410-419
Supplementary European Search Report for Application No. EP08796044, dated Jul. 30, 2010, 8 pages.
Tomoeda K., et al., "Mutations in the 4-Hydroxyphenylpyruvic Acid Dioxygenase Gene Are Responsible for Tyrosinemia Type III and Hawkinsinuria," Molecular Genetics and Metabolism, 2000, vol. 71 (3), pp. 506-510.
Van Eijik H.M., et al., "Determination of Amino Acid Isotope Enrichment Using Liquid Chromatography-Mass Spectrometry," Analytical Chemistry, 1999, vol. 271 (1), pp. 08-17.
Wise J.K., et al., "Influence of Glucocorticoids on Glucagon Secretion and Plasma Amino Acid Concentrations in Man," The Journal of Clinical Investigation, 1973, vol. 52 (11), pp. 2774-2782.
Written Opinion for Application No. PCT/US08/68653, dated Sep. 15, 2008, 4 Pages.
Yamamoto A., et al., "Steroid Hormone Profiles of Urban and Tidal Rivers Using LC/MS/MS Equipped with Elextrospray Ionization and Atmospheric Pressure Photoinization Sources," Envrionmental Science and Technology, 2006, vol. 40 (13), pp. 4132-4137.
Yang W.C., et al., "Enhancement of Amino Acid Detection and Quantification by Electrospray Ionization Mass Spectrometry," Analytical Chemistry, 2006, vol. 78 (13), pp. 4702-4708.
Zhi-Yi T., et al., "Meaurement of Free Amino Acid of Biological Fluids by reversed—phase HPLC and clinical application," Chinese Journal of Medical Laboratory Sciences, 1994, pp. 140-143.
Extended European Search Report for Application No. 18212925.4, dated Aug. 22, 2019.
Abbas A.K., et al., "S-Sulfo-Cysteine is an Endogenous Amino Acid in Neonatal Rat Brain but an Unlikely Mediator of Cysteine Neurotoxicity," Neurochemical Research, 2008, vol. 33 (2), pp. 301-307.
Aebersold R., et al., "Mass Spectrometry-Based Proteomics," Nature, 2003, vol. 422 (6928), pp. 198-207.
Andrensek S., et al., "Determination of Phenylalanine and Tyrosine by Liquid Chromatography/Mass Spectrometry," Journal of AOAC International, 2003, vol. 86 (4), pp. 753-758.
Annual Report ERNDIM-EQAS 2007.
Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.
Biochrom 30 Amino Acid System. Retrieved from the Internet:[URL:http://www.biochrom.co.uk/download/6/Biochrom%2030/020AminocY020Acid%20AnalysercY020Brochure .pdf].
Bures E.J., et al., "Synthesis of the Protein-Sequencing Reagent4-(3-Pyridinylmethylaminocarboxypropyl) phenyl Isothiocyanate and characterization of 4-(3-Pyridinylmethylaminocarboxypropyl) Phenylthiohydantoins," Analytical Biochemistry, 1995, vol. 224 (1), pp. 364-372.
Carey F.A. "Organic Chemistry", 1992, McGraw Hill, Inc., p. 1111.

Casetta B., et al., "Development of a Method for Rapid Quantitation of Amino Acids by Liquid Chromatography Tandem Mass Spectrometry (LC-MSMS) In Plasma," Clinical Chemistry and Laboratory Medicine, 2000, vol. 38 (5), pp. 391-401.
Chace D.H., et al., "Rapid Diagnosis of Maple Syrup Urine Disease in Blood Spots from Newborns by Tandem Mass Spectrometry," Clinical Chemistry, 1995, vol. 41 (1), pp. 62-68.
Coloso R.M., et al., "Metabolism of Cyst(e)ine in Rat Enterocytes," Journal of Nutrition, 1989, vol. 119 (12), pp. 1914-1924.
Coppex M.L. "Derivatives for HPLC Analysis," Diploma Thesis, Nov. 1999-Feb. 2000, pp. 1-68.
Description of Service Schedule and Guidelines for Sample Shipment. Medical Genetics Program, Duke University Medical Center [Online],2008, Retrieved from the Internet:, http://medgenetics.pediatrics.duke.edu/wysiwyg/downloads/Mass_Spec_Sample_and_Shipping_info_091208.pdf.
Extended European Search Report for Application No. 08796044.9, dated Jul. 30, 2010.
Extended European Search Report for Application No. EP16167897, dated Jul. 6, 2016, 12 pages.
Extended European Search Report for Application No. EP16188837.5, dated Nov. 10, 2016, 10 pages.
Final Office Action dated Aug. 3, 2017 for U.S. Appl. No. 14/635,730, filed Mar. 2, 2015.
Final Office Action dated Jan. 5, 2012 for U.S. Appl. No. 12/646,666, filed Dec. 23, 2009.
Final Office Action dated Oct. 15, 2008 for U.S. Appl. No. 10/963,442, filed Oct. 12, 2004.
Fonteh A.N., et al., "Free Amino Acid and Dipeptide Changes in the Body Fluids from Alzheimer's Disease Subjects," Amino Acids, 2007, vol. 32 (2), pp. 213-224.
Green A., "Plasma Amino Acids in a Patient with Wilson's Disease Presenting with an Acute Haemolytic Anaemia," Journal of Inherited Metabolic Disease, 1981, vol. 4 (1), pp. 33-36.
Guan X., et al., "A Simultaneous Liquid Chromatography/Mass Spectrometric Assay of Glutathione, Cysteine, Homocysteine and their Disulfides in Biological Samples," Journal of Pharmaceutical and Biomedical Analysis , 2003, vol. 31 (2), pp. 251-261.
Henderson, Amino Acid Pot Pourri, Department of Clinical Biology at St. James 19s University Hospital [Online], Jun. 2009. Retrieved from the Internet:, at http://www.metbio.net/docs/MetBio-Presentation-KABU556300-13-06-2009.pdf, 30 pages.
Hernanz A., et al., "Increased Plasma Levels of Homocysteine and Other Thiol Compounds in Rheumatoid Arthritis Women," Clinical Biochemistry, 1999, vol. 32 (1), pp. 65-70.
Hess D., et al., "Liquid Chromatography-Electrospray Ionization Mass Spectrometry of 4-(3-Pyridinylmethylaminocarboxypropyl) Phenylthiohydantoins," Analytical Biochemistry, 1995, vol. 224 (1), pp. 373-381.
Hess S., et al., "Acid Hydrolysis of Silk Fibroins and Determination of the Enrichment of Isotopically Labeled Amino Acids Using Precolumn Derivatization and High-Performance Liquid Chromatography-Electrospray Ionization-Mass Spectrometry," Analytical Biochemistry, 2002, vol. 311 (1), pp. 19-26.
Hess S., et al., "Chirality Determination of Unusual Amino Acids Using Precolumn Derivatization and Liquid chromatography-Electrospray Ionization Mass Spectrometry," Journal of Chromatography, 2004, vol. 1035 (2), pp. 211-219.
International Search Report for Application No. PCT/US08/68653, dated Sep. 15, 2008, 2 Pages.
Ji Y., et al., "Determination of Phenethyl Isothiocyanate in Human Plasma and Urine by Ammonia Derivatization and Liquid Chromatography-Tandem Mass Spectrometry," Analytical Biochemistry, 2003, vol. 323 (1), pp. 39-47.
Kaye C.I. and The Committee on Genetics, "Technical Report: NewBorn Screening Fact Sheets," Pediatrics, 2006, vol. 116, pp. e934-e963.
Knapp D.R., "Amino Acids and Peptides" in: Handbook of Analytical Derivatization Reactions, John Wiley & Sons, New York, 1979, p. 281.
Kramarenko G.G., et al., "Pecularities of Carnosine Metabolism in a Patient with Pronouced Homocamosinemia," Bulletin of Experimental Biology and Medicine, 2001, vol. 132 (4), pp. 996-999.

(56) References Cited

OTHER PUBLICATIONS

Lee J.C., et al., "Plasma Amino Acid Levels in Patients with Colorectal Cancers and Liver Cirrhosis with Hepatocellular Carcinoma," Hepatogastroenterology, 2003, vol. 50 (53), pp. 1269-1273.

Lee Y.H., et al., "Highly Informative Proteome Analysis by Combining Improved N-Terminal Sulfonation for De Novo Peptide Sequencing and Online Capillary Reverse-Phase Liquid Chromatography/Tandem Mass Spectrometry," Proteomics, 2004, vol. 4 (6), pp. 1684-1694.

Lehmann W.D., et al., "Assay for Plasma Free Phenylalanine and Tyrosine by High-pressure Liquid Chromatography and Field Desorption Mass Spectrometry and its Application to an in Vivo Study of the Phenylalanine Hydroxylating System in Man," Biomedical Mass Spectrometry, 1981, vol. 8 (12), pp. 598-605.

Leinonen A., et al., "Liquid Chromatography/Mass Spectrometry in Anabolic Steroid Analysis-Optimization and Comparison of Three Ionization Techniques: Electrospray Ionization, Atmospheric Pressure Chemical Ionization and Atmospheric Pressure Photoionization," Journal of Mass Spectrometry, 2002, vol. 37 (7), pp. 693-698.

Li et al, CE and CE/MS for Natural Products, Agilent Technologies, Jan. 3, 2009, 12 pgs.

Lida T., et al., "Complete Enantiomeric Separation of Phenylthiocarbamoylated Aminoa Acids on a Tandem Column of Reversed and Chiral Stationary Phases," Analytical Chemistry, 1997, vol. 69 (21), pp. 4463-4468.

Liu Z., et al., "Derivitization of Amino Acids with N, N-Dimethyl-2, 4-Dinitro-5-Fluorobenzylamine for Liquid Chromatography/Electrospray Ionization Mass Spectrometry," Rapid Communications in Mass Spectrometry, 2004, vol. 18 (10), pp. 1059-1065.

Martens-Lobenhoffer J., et al., "Simultaneous Detection of Arginine, Asymmetric Dimethylarginine, Symmetric Dimethylarginine and Citrulline in Human Plasma and Urine Aplying Liquid Chomatographymass Spectrometry with Very Straightforward Sample Preparation," Journal of Chromatography B, 2003, vol. 798 (2), pp. 231-239.

Mass Spectroscopy in Chromatography, Translation of Analytical Chemistry II (Revised 3rd Ed.), Apr. 10, 1992, 2 Pages.

Moyano D., et al., "Plasma Amino Acids in Anorexia Nervosa," European Journal of Clinical Nutrition, 1998, vol. 52 (9), pp. 684-689.

Nakamura T., et al., "Increased Plasma Gluconeogenic and System A Amino Acids in Patients with Pancreatic Diabetes due to Chronic Pancreastitis in Comparision with Primary Diabetes," The Tohoku Journal of Experimental Medicine, 1994, vol. 173 (4), pp. 413-420.

Non-Final Office Action dated Jul. 8, 2011 for U.S. Appl. No. 12/646,666, filed Dec. 23, 2009.

Non-Final Office Action dated Jan. 10, 2008 for U.S. Appl. No. 10/963,442, filed Oct. 12, 2004.

Non-Final Office Action dated Dec. 27, 2016 for U.S. Appl. No. 14/635,730, filed Mar. 2, 2015.

Non-Final Office Action dated Feb. 28, 2018 for U.S. Appl. No. 14/635,730, filed Mar. 2, 2015.

Non-Final Office Action dated Mar. 28, 2014 for U.S. Appl. No. 12/646,666, filed Dec. 23, 2009.

Non-Final Office Action dated Mar. 30, 2009 for U.S. Appl. No. 10/963,442, filed Oct. 12, 2004.

Notice of Allowance dated Oct. 25, 2018 for U.S. Appl. No. 14/635,730, filed Mar. 2, 2015.

\* cited by examiner

| #Analyte | Analyte *=split peak | MW | PITC | AA(MW)+PITC (derivatization) | RetTime | Ions Obs'd |
|---|---|---|---|---|---|---|
| 18 | Phosphoserine | 185.1 | 135.19 | 320.29 | 2.648 | 319,639 |
| 1 | Aspartic Acid | 133.1 | 135.19 | 268.29 | 2.822 | 267 |
| 2 | Glutamic Acid | 147.13 | 135.19 | 282.32 | 3.230 | 281 |
| 42 | Argninosuccinic Acid | 290.3 | 135.19 | 425.49 | 3.448 | 424,849 |
| 19 | L-alpha-aminoadipic Acid | 161.2 | 135.19 | 296.39 | 4.004 | 295 |
| 20 | Hydroxy-L-Proline | 131.1 | 135.19 | 266.29 | 4.588 | 265,531 |
| 22 | Asparagine | 132.12 | 135.19 | 267.31 | 5.469 | 266,533 |
| 3 | Serine | 105.09 | 135.19 | 240.28 | 5.763 | 239,479 |
| 23 | Glutamine | 146.1 | 135.19 | 281.29 | 6.129 | 280 |
| 4 | Glycine | 75.07 | 135.19 | 210.26 | 6.333 | 209,419 |
| 24 | Beta-Alanine | 89.09 | 135.19 | 224.28 | 6.802 | 223,447 |
| 25 | Sarcosine (Sarc) | 89.09 | 135.19 | 224.28 | 6.940 | 223 |
| 26 | Taurine | 125.1 | 135.19 | 260.29 | 7.311 | 259,519 |
| 5 | Histidine | 155.16 | 135.19 | 290.35 | 7.444 | 289,579 |
| 27 | Citrulline | 175.2 | 135.19 | 310.39 | 7.643 | 309,619 |
| 33 | GABA | 103.1 | 135.19 | 238.29 | 8.140 | 237,475 |
| 8 | Arginine | 174.2 | 135.19 | 309.39 | 8.714 | 308,617 |
| 6 | Threonine | 119.12 | 135.19 | 254.31 | 8.735 | 253,507 |
| 34 | Carnosine | 226.2 | 135.19 | 361.39 | 8.882 | 360,721 |
| 28 | DL-Beta-Aminoisobutyric Acid | 103.1 | 135.19 | 238.29 | 9.425 | 237,475 |
| 7 | Alanine | 89.09 | 135.19 | 224.28 | 9.449 | 223,447 |
| 39 | DL(+)-Allo-Gamma-Hydroxylysine | 162.2 | 135.19 | 297.39 | 10.373 | 295 |
| 9 | Proline | 115.13 | 135.19 | 250.32 | 10.514 | 249 |
| 36 | L-3-Methylhistidine | 169.2 | 135.19 | 304.39 | 10.773 | 303,607 |
| 37 | Anserine | 240.26 | 135.19 | 375.45 | 10.980 | 374,749 |
| 35 | L-1-Methylhistidine | 169.2 | 135.19 | 304.39 | 11.348 | 303,607 |
| 38 | Ethanolamine | 61.08 | 135.19 | 196.27 | 11.923 | 195 |
| 44 | L-Cysteine | 121.2 | 135.19 | 256.39 | 12.468 | 255,511 ** |
| 29 | L-alpha-Amino-N-Butyric Acid | 103.1 | 135.19 | 238.29 | 12.513 | 237,475 |
| 43 | E-Amino-n-Caproic Acid | 131.2 | 135.19 | 266.39 | 12.796 | 265,531 |
| 10 | Tyrosine | 181.19 | 135.19 | 316.38 | 13.692 | 315,631 |
| 30 | DL-Allo-Cystathionine* | 222.3 | 135.19 | 357.49 | 15.200 | 491 |
| 11 | Valine | 117.15 | 135.19 | 252.34 | 15.639 | 251,503 |
| 12 | Methionine | 149.21 | 135.19 | 284.4 | 15.728 | 283,567 |
| 13 | Cystine* | 240.3 | 135.19 | 375.49 | 16.030 | 509 |
| 14 | Isoleucine | 131.17 | 135.19 | 266.36 | 18.606 | 265,531 |
| 41 | L-allo-Ile | 131.2 | 135.19 | 266.39 | 18.713 | 265,531 |
| 15 | Leucine | 131.17 | 135.19 | 266.36 | 18.741 | 265,531 |
| 40 | Ornithine | 132.16 | 135.19 | 267.35 | 18.978 | 401,803 |
| 32 | Tryptophan | 204.23 | 135.19 | 339.42 | 18.996 | 338,677 |
| 16 | Phenylalanine | 165.19 | 135.19 | 300.38 | 19.112 | 299,599 |
| 17 | Lysine | 146.19 | 135.19 | 281.38 | 19.338 | 415,831 |
| 31 | Homocystine | 135.2 | 135.19 | 270.39 | 20.053 | 269 |
| 21 | Phosphoethanolamine (PEA) | 141.1 | 135.19 | 278.29 | | |

FIG. 1

ANALYSIS OF AMINO ACIDS IN BODY FLUID BY LIQUID CHROMOTOGRAPHY-MASS SPECTROMETRY

CROSS REFERENCE TO RELATED PATENT APPLICATIONS

This application is a continuation of U.S. application Ser. No. 14/635,730, filed Mar. 2, 2013 (issued as U.S. Pat. No. 10,175,208), which is a continuation of U.S. application Ser. No. 12/646,666, filed Dec. 23, 2009 (issued as U.S. Pat. No. 8,969,089 on Mar. 3, 2015), which is a continuation-in-part of U.S. application Ser. No. 10/963,442, filed Oct. 12, 2004, and a continuation-in-part of International Patent Appl. No. PCT/US2008/068653, filed Jun. 27, 2008, which claims priority to U.S. Appl. No. 60/947,338, filed Jun. 29, 2007, each of which is hereby incorporated by reference in its entirety.

FIELD OF THE INVENTION

The present invention relates generally to the detection and analysis of amino acids, particularly amino acids contained in biological fluids.

BACKGROUND

The identity and amount of amino acids in a patient's body fluid (e.g., plasma) is important in a patient's health for a number of reasons. Aberrant amino acid levels can be used to diagnose disease or illness. For example, low plasma amino acid levels may occur in patients with cancer, anorexia, arthritis, folliculitis, alcohol abuse, glucagonoma, and/or pregnancy. Patients undergoing stress or depression may also have low plasma amino acid levels. In particular, depressed patients may be deficient in phenylalanine, tyrosine, methionine, glycine, tryptophan, and/or taurine. Psychotic patients may have low levels of amino acids such as glycine, tryptophan, and/or histidine and elevated levels of amino acids such as phenylalanine, tyrosine, and/or serine.

Patients with infectious disease and/or fever also may have reduced amino acid levels, although some amino acids in such patients such as phenylalanine may be present at elevated levels. Patients with kidney failure may have low levels of amino acids such as tyrosine, threonine, leucine, isoleucine, valine, lysine, and/or histidine. Patients with Crohn's disease, ulcerative colitis, chronic fatigue syndrome may have abnormally low levels of cystine and glutamine in their plasma.

In addition, amino acid levels that are higher than normal may be indicative of a disease state. For example, elevated plasma amino acid levels may be observed in patients with liver disease, pancreatitis, heavy metal poisoning, vitamin C deficiency, and/or vitamin D deficiency. In particular, patients with Wilson's disease may exhibit elevated levels of tryptophan and histidine. Patients with Cushing's disease or gout may exhibit elevated alanine levels. Diabetic patients may exhibit elevated levels of valine, leucine, and/or isoleucine. Hyperactive children may exhibit elevated levels of tyrosine and phenylalanine. Patients with Maple Syrup Urine Disease may have elevated levels of leucine, isoleucine, and valine in their plasma. As such, methods for analyzing amino acids in body fluids such as plasma are useful in medicinal and scientific settings.

Traditionally, analytical methods for amino acids have included a derivatization step. During derivatization, the amino acid is reacted with a derivatizing reagent that facilitates analysis of amino acids in the sample. Derivatizing agents typically react with the free amino groups of amino acids in the sample. Common reagents for derivatizing amino acids include isothiocyanates (e.g., phenyl isothiocynate (PITC)), o-phthaldialdehyde (OPA), 2,4-dinitrofluorobenzene (DNFB), and N$\alpha$-(2,4-dinitro-5-fluorophenyl)-L-alainamide (FDAA). Derivatizing agents are useful because they may include substituents that facilitate analysis of the derivatized amino acid. For example, derivatizing agents may include chromophores for UV-absorption detection or fluorophores for fluorescent detection.

Derivatized amino acids may be separated and detected by performing chromatography such as liquid chromatography (LC) or gas chromatography (GC), coupled with mass spectrometry (i.e., LC-MS or GC-MS). Amino acids, however, have diverse chemical structures (e.g., basic, acidic, aromatic, polar, non-polar, etc.), and because of significant differences in the chemical structures of various amino acids that may be present in body fluids, these compounds present a difficult task for analysts to solve in regard to derivatization/separation in LC-MS or GC-MS.

Methods for detecting amino acids using LC and MS have been reported and include, for example, Casetta et al. "Development of a method for rapid quantification of amino acids by liquid chromatography, tandem mass spectrometry (LC-MSMS) in plasma" Clin Chem Lab Med (2000) 38: 391-401; Hess et al, "Acid hydrolysis of silk fibroins and determination of the enrichment of isotopically labeled amino acids using precolumn derivatization and high performance liquid chromatography-electrospray ionization mass spectrometry" Anal Biochem (2002) 311:19-26; Ji et al., "Determination of phenethyl isothiocyanate in human plasma and urine by ammonia derivatization and liquid chromatography-tandem mass spectrometry" Anal Biochem (2003) 323:39-47; Van Eijik et al., "Determination of amino acid isotope enrichment using liquid chromatography-mass spectrometry" (1999) Anal Biochem 271:8-17; and Liu et al. "Derivatization of amino acids with N,N-dimethyl-2,4-dinitro-5-fluorobenzylamine for liquid chromatography/electrospray ionization mass spectrometry" (2004) Rapid Commun Mass Spectrom 18:1059-65. Improved methods for detecting amino acids in body fluids are desirable.

SUMMARY OF THE INVENTION

Disclosed are methods for detecting various individual amino acids that may be present in a body fluid of an individual. Detection of the individual amino acids in the body fluid may be used to determine whether the body fluid contains an abnormal of one or more amino acids. In one aspect, the method involves derivatizing the body fluid amino acids, separating the derivatized amino acids by liquid chromatography (LC), identifying the derivatized amino acids using mass spectrometry (MS) analysis, and quantifying the derivatized amino acid by comparison to structurally similar amino acids from a set of amino acids standards. Preferably, the MS is other than tandem MS including, for example, single MS. Structurally similar amino acids share significant structural characteristics such as key functional groups such that the identification of one amino acid by mass spectrometry can be used to identify the other structurally similar amino acid in the same method. The set of individual amino acid standards is preferably used as a set of internal standards by adding the set to the body fluid prior to processing.

Suitable body fluids include, for example, plasma, serum, saliva, urine, and cerebral spinal fluid (CSF). For methods in which individual amino acids are detected, identified, and/or quantified in plasma, the levels may be compared to the reference ranges provided in Table 1. Plasma amino acid levels that fall outside of the reference ranges of Table 1 may be identified as abnormal. For methods in which individual amino acids are detected, identified, and/or quantified in urine, the levels may be compared to the reference ranges provided in Table 2. Urine amino acid levels that fall outside of the reference ranges of Table 2 may be identified as abnormal. For methods in which individual amino acids are detected, identified, and/or quantified in CSF, the levels may be compared to the reference ranges provided in Table 3. CSF amino acid levels that fall outside of the reference ranges of Table 3 may be identified as abnormal. For methods in which individual amino acids are detected, identified, and/or quantified in saliva, the levels may be compared to the reference ranges provided in Table 4. Saliva amino acid levels that fall outside of the reference ranges of Table 4 may be identified as abnormal. In some embodiments, the reference range for each amino acid varies based on the age of the subject (i.e., neonate, infant, child, or adult).

The set of standards may be non-derivatized and added to the starting body fluid or to any post processing step prior to derivatization. In a preferred embodiment, the standards comprise individual deuterated amino acids (i.e., single amino acids containing one or more deuterium ions). The set of standards also may be added to the body fluid amino acids after the step of derivatization. In this case, the added standards should be derivatized in the same manner as the body fluid amino acids. In one approach, the amino acids are derivatized with an isothiocyanate (e.g., phenyl isothiocynate (PITC). In a preferred embodiment, the derivatizing agent is PITC. Other suitable derivatizing agents may include o-phthaldialdehyde (OPA), 2,4-dinitrofluorobenzene (DNFB), and Nα-(2,4-dinitro-5-fluorophenyl)-L-alainamide (FDAA).

The amount of each identified amino acid from a volume of body fluid can be determined by comparing the signal by MS to the signal of a known amount of structurally similar amino acid. The amount of the amino acid in the body fluid can then be expressed relative to the volume of body fluid analyzed to obtain a concentration of the amino acid in the original body fluid. Quantitative analysis is preferably done with internal standards.

In some embodiments, the body fluid can be processed to obtain a fraction with an enriched concentration of amino acids prior to further analysis. In one approach, a low molecular weight fraction of the body fluid is obtained (e.g., by passing the bodily fluid through a molecular weight filter).

In one embodiment, the method may be used to detect at least 20 different individual amino acids. In other embodiments, the method may be used to detect at least 25, 30, 35, or 40 individual amino acids.

For example, the method may be useful for detecting and/or quantifying any combination of the individual amino acids including, but not limited to, phosphoserine, sulfo-cysteine, arginosuccinic acid, hydroxyproline, aspartic acid, asparagine, glutamic acid, serine, phosphoethanolamine (PEA), glutamine, glycine, histidine, sarcosine, taurine, carnosine, citrulline, arginine, anserine, 1-methyl-histidine, 3-methyl-histidine, alpha-amino-adipic acid (AAD), threonine, alanine, beta-alanine (BALA), proline, ethanolamine, gamma-amino-butyric acid (GABA), beta-amino-isobutyric acid (BAIA), alpha-amino-butyric acid (AAB), cysteine, tyrosine, valine, methionine, L-allo-cystathionine (cystathionine-A), L-cystathionine (cystathionine-B), cystine, iso-leucine, allo-isoleucine, leucine, DL-hydroxylysine (hydroxylysine (1)), DL-allo-hydroxylysine (hydroxylysine (2)), phenylalanine, ornithine, tryptophan, homocystine, arginosuccinic acid (ASA), lysine, and Hawkinsin ((2-L-cystein-S-yl-1,4-dihydroxycyclohex-5-en-1-yl)-acetic acid). In addition, the method may be used to diagnose a disease state based on the level of any of the detected individual amino acids in body fluid.

In one embodiment, the method may be useful for detecting and/or quantifying any combination of the individual amino acids including, but not limited to, aspartic acid, ASA, sulfo-cysteine, glutamic acid, OH-proline, serine, asparagine, PEA, AAD, glycine, glutamine, sarcosine, histidine, beta-alanine, taurine, citrulline, carnosine, threonine, arginine, anserine, 1-methyl-histidine, 3-methyl-histidine, alanine, GABA, BAIB, proline, ethanolamine, AAB, tyrosine, valine, methionine, cystathionine A, cystathionine B, cystine, isoleucine, allo-isoleucine, leucine, OH-lysine-1, OH-lysine-2, homocystine, phenylalanine, tryptophan, ornithine, and lysine.

In another embodiment, the method may be useful for detecting and/or quantifying any combination of the individual amino acids including, but not limited to, hydroxyproline, aspartic acid, asparagine, glutamic acid, serine, glutamine, glycine, histidine, sarcosine, taurine, citrulline, arginine, 1,3-methyl-histidine, alpha-amino-adipic acid, threonine, alanine, beta-alanine, proline, ethanolamine, gamma-amino-butyric acid, beta-amino-isobutyric acid, alpha-amino-butyric acid, tyrosine, valine, methionine, L-cystathionine, isoleucine, leucine, phenylalanine, ornithine, tryptophan, homocystine, and lysine.

In yet another embodiment, the method may be useful for detecting and/or quantifying any combination of the individual amino acids including, but not limited to, hydroxyproline, aspartic acid, asparagine, glutamic acid, serine, glutamine, glycine, histidine, sarcosine, taurine, citrulline, arginine, 1,3-methyl-histidine, alpha-amino-adipic acid, threonine, alanine, beta-alanine, proline, ethanolamine, gamma-amino-butyric acid, beta-amino-isobutyric acid, alpha-amino-butyric acid, tyrosine, valine, methionine, L-cystathionine, isoleucine, leucine, phenylalanine, ornithine, tryptophan, homocystine, lysine, cystine, and hydroxylysine.

In still another embodiment, the method may be useful for detecting and/or quantifying any combination of the individual amino acids including, but not limited to, hydroxyproline, aspartic acid, asparagine, glutamic acid, serine, glutamine, glycine, histidine, sarcosine, taurine, citrulline, arginine, alpha-amino-adipic acid, threonine, alanine, beta-alanine, proline, gamma-amino-butyric acid, beta-amino-isobutyric acid, alpha-amino-butyric acid, tyrosine, valine, methionine, isoleucine, leucine, phenylalanine, ornithine, tryptophan, homocystine, and lysine.

In one embodiment, the method may be useful for detecting and/or quantifying any combination of the individual amino acids including, but not limited to, phosphoserine, sulfo-cysteine, arginosuccinic acid, hydroxyproline, aspartic acid, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, allo-isoleucine, DL-hydroxylysine, DL-allo-hydroxylysine, and homocystine.

In another embodiment, the method may be useful for detecting and/or quantifying any combination of the individual amino acids including, but not limited to, phosphoserine, sulfo-cysteine, arginosuccinic acid, hydroxyproline, aspartic acid, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, DL-hydroxylysine, DL-allo-hydroxylysine, and homocystine. In a further embodiment, the method can be used to identify any of cysteine, phosphoserine or arginosuccinic acid.

In a further embodiment, the method may be useful for detecting and/or quantifying any combination of the individual amino acids including, but not limited to, phosphoserine, sulfo-cysteine, arginosuccinic acid, hydroxyproline, phosphoethanolamine, sarcosine, carnosine, anserine, 1,3-methyl-histidine, alpha-amino-adipic acid, beta-alanine, proline, ethanolamine, gamma-amino-butyric acid, beta-amino-isobutyric acid, cysteine, L-allo-cystathionine-A, L-cystathionine, cystine, allo-isoleucine, DL-hydroxylysine, DL-allo-hydroxylysine, and homocystine.

In a further embodiment, the method may be useful for detecting and/or quantifying any combination of the individual amino acids including, but not limited to, phosphoserine, sulfo-cysteine, arginosuccinic acid, hydroxyproline, phosphoethanolamine, sarcosine, carnosine, anserine, 1,3-methyl-histidine, alpha-amino-adipic acid, ethanolamine, gamma-amino-butyric acid, beta-amino-isobutyric acid, L-allo-cystathionine-A, L-cystathionine, cystine, allo-isoleucine, DL-hydroxylysine, DL-allo-hydroxylysine, and homocystine.

In a further embodiment, the method may be useful for detecting and/or quantifying any combination of the individual amino acids including, but not limited to, phosphoserine, cysteine, arginosuccinic acid, hydroxyproline, phosphoethanolamine, sarcosine, carnosine, anserine, 1,3-methyl-histidine, alpha-amino-adipic acid, ethanolamine, gamma-amino-butyric acid, beta-amino-isobutyric acid, L-allo-cystathionine-A, L-cystathionine, cystine, DL-hydroxylysine, DL-allo-hydroxylysine, and homocystine.

As used herein, "sulfo-cysteine" is a short-hand representation recognized in the art for a single amino acid, L-cysteine-S-sulfate, which may also be referred to as S-sulfo-L-cysteine, S-sulfo-cysteine, S-sulfocysteine, and sulfocysteine. Sulfo-cysteine has the structure CyS-SO$_3$H. See e.g., Abbas, et al., *S-Sulfo-Cysteine is an Endogenous Amino Acid in Neonatal Rat Brain but an Unlikely Mediator of Cysteine Neurotoxicity*, Neurochemical Research (2008), 33:301-307 (which uses the term S-sulfo-cysteine); Coloso, et al., *Metabolism of Cyst(e)ine in Rat Enterocytes*, J. Nutrition (1989), 119:1914-1924 (which uses the term sulfocysteine throughout the article); Henderson, Amino Acid Pot Pourri, Department of Clinical Biology at St. James's University Hospital (which uses the terms S-sulfocysteine (for example on p. 16), sulfocysteine (on p. 18 and 20), and sulfocys (on p. 19) to indicate the same amino acid); Parvy, et al., *A New Pitfall in Plasma Amino Acid Analysis*, Clinical Chem. (1989), p. 178 (which uses the term sulfocysteine); Description of Service Schedule and Guidelines for Sample Shipment, Medical Genetics Program, Duke University Medical Center (which indicates a test is available for sulfocysteine in urine, p. 4); The Biochrom 30 Amino Acid System product brochure (which indicates on p. 9 that the instrument may be used to measure sulfocysteine); and the Annual Report ERNDIM-EQAS 2007 (which indicates on p. 2 that sulphocysteine is available for purchase from Sigma-Aldrich under catalog number C2196 (which is the catalog number for L-Cysteine S-Sulfate)).

In other embodiments, the method quantifies at least two, at least three, at least four, at least five, at least seven, at least ten, at least fifteen, at least twenty, at least twenty five, or at least thirty or more individual amino acids.

The disclosed methods may be used as a basis for diagnosis, or for monitoring the effectiveness of treatment for a variety of diseases known to be associated with abnormal levels of individual amino acid (i.e., single amino acids apart from dipeptides and polypeptides). For example, the levels of leucine, isoleucine, valine, lysine, and/or histidine may be used to diagnose and/or monitor kidney failure; cystine and/or glutamine may be used to diagnose and/or monitor Crohn's disease, ulcerative colitis, and/or chronic fatigue syndrome; tryptophan and/or histidine may be used to diagnose and/or monitor Wilson's disease; alanine may be used to diagnose and/or monitor Cushing's disease or gout; valine, leucine, and/or isoleucine may be used to diagnose and/or monitor diabetes and/or Maple Syrup Urine Disease; tyrosine and/or phenylalanine may be used to diagnose and/or monitor hyperactivity disorders; and hawkinsin may be used to diagnose and/or monitor hawkinsinuria.

LC separation of derivatized amino acids may be performed using any type of LC system such as are commercially available. A suitable LC column is one that has a packing material which includes minute particles (e.g., silica particles having a diameter of about 2-5 μm, and preferably about 3 μm). The particles typically have pores of about 50 to 300 angstroms, and preferably about 150 angstroms. The particles typically have a surface area of about 50-600 m$^2$/g, and preferably about 100 m$^2$/g.

The particles may include a hydrophobic stationery phase bonded to their surface. In one embodiment, the hydrophobic stationery phase may be an alkyl phase, which may include C-4, C-8, and C-18 (preferably C-18).

The column may have any suitable dimensions. Preferably, the column has a diameter of about 0.5 mm to about 5 mm and a length of about 15 mm to about 300 mm, and most preferably, a diameter of about 2 mm and a length of about 50 mm.

LC separation of derivatized amino acids may also be performed using a hydrophobic solvent or a solvent mixture that includes a hydrophobic solvent in a gradient as a mobile phase to elute the amino acids. In one embodiment, the derivatized fraction may be applied to the column in an aqueous buffer (i.e., a hydrophilic solvent) and the amino acids may be eluted by applying a mobile phase to the column that has an increasing amount of organic solvent (i.e., a hydrophobic solvent). For example, the aqueous buffer may include (95% H$_2$O, 5% acetonitrile), and the amino acids may be eluted from the column by gradually increasing the concentration of acetonitrile to about 100% in the mobile phase. If desirable, the mobile phase may be heated to a temperature of about 40-60° C., preferably about 50° C. In addition, the mobile phase may optionally include one or more additional reagents that are useful during LC and/or MS. For example, ammonium acetate or acetic acid.

MS analysis of derivatized amino acids may be performed by ionization of the sample. Suitable ionization techniques include electrospray ionization (ESI), atmospheric pressure chemical ionization (APCI), photoinonization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. Preferably, MS is performed using ESI. Further, MS may be performed using a negative or positive ion mode, and preferably a negative ion mode.

MS analysis of derivatized amino acids may be performed with any of several types of ion analyzers including quadrupole analyzers, ion traps analyzers, and time-of-flight analyzers. Preferably, MS may be performed using a quadrupole analyzer. The ions generated during MS may be detected by using several detection modes including selective ion monitoring mode (SIM) and scanning mode. Preferably, the ions are detected by using SIM. MS is preferably other than tandem MS.

Also provided is a method of diagnosing the existence of a metabolic disorder involving amino acid metabolism in an individual. The method comprises determining if a body fluid contains an abnormal level of one or more amino acids by first (a) derivatizing the body fluid amino acids; (b) separating the derivatized amino acids by liquid chromatography (LC); (c) subjecting the separated derivatized amino acids to mass spectroscopic analysis (MS) using a mass spectrometer; and (d) using the MS analysis to identify the amount of derivatized amino acids from the body fluid by comparing to structurally similar amino acids from a set of amino acid standards. Various embodiments of this method are similar to those already discussed.

BRIEF DESCRIPTION OF THE FIGURES

FIG. 1 is a table showing various amino acids detected and quantifying by the methods described herein. Third column indicates MW "molecular weight"; fourth column indicates PITC molecular weight; fifth column indicates molecular weight of each PITC derivatized amino acids; six column is the LC retention time; seventh column indicates mass spectrometry ions observed.

DETAILED DESCRIPTION OF THE PREFERRED EMBODIMENTS

Figure 2:
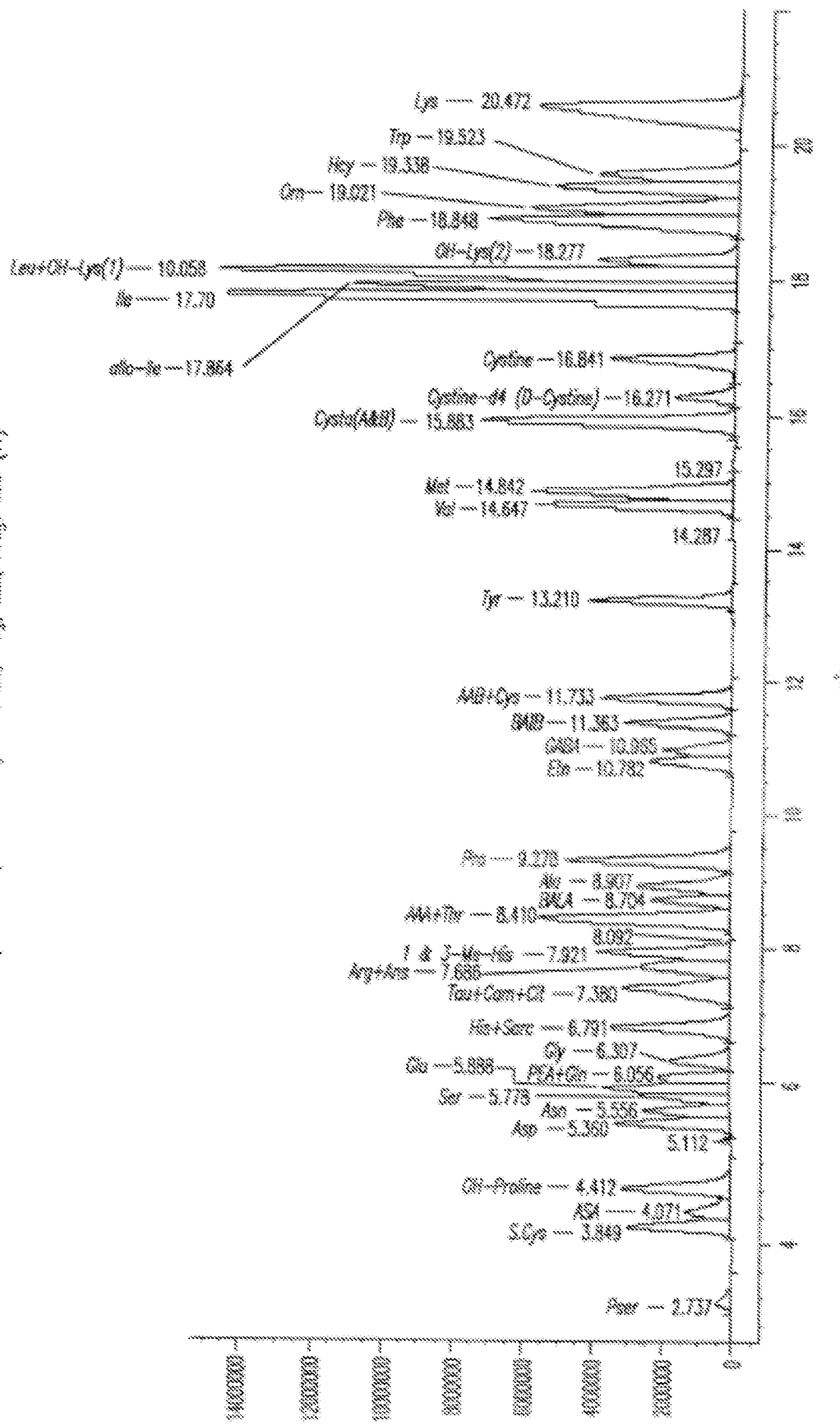
FIG. 2 shows the results of an MS analysis of a single sample containing the indicated amino acids, previously subject to LC. The ion size characteristic of each amino acid is indicated.

As used herein, "amino acid" means any molecule that includes an alpha-carbon atom covalently bonded to an amino group and an acid group. The acid group may include a carboxyl group. "Amino acid" may include molecules having one of the formulas:

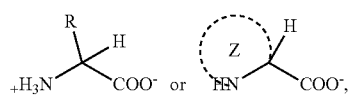

wherein R is a side group and Z includes at least 3 carbon atoms. "Amino acid" includes, but is not limited to, the twenty endogenous human amino acids and their derivatives such as lysine, asparagine, threonine, serine, isoleucine, methionine, proline, histidine, glutamine, arginine, glycine, aspartic acid, glutamic acid, alanine, valine, phenylalanine, leucine, tyrosine, cysteine, tryptophan, phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (1)), DL-allo-hydroxylysine (hydroxylysine (2)), ornithine (ORN), homocystine (HCY), and derivatives thereof. "Amino acids" also includes stereoisomers such as the D-amino acid and L-amino acid forms. Unless specifically indicated otherwise, the term "amino acid" refers to the individual (i.e., free) amino acid molecules apart from amino acids present in dipeptides, polypeptides, and proteins.

As used herein, "body fluid" means any fluid that can be isolated from the body of an individual. For example, "body fluid" may include blood, plasma, serum, bile, saliva, urine, tears, perspiration, cerebrospinal fluid (CSF), and the like. Preferably the body fluid is plasma, serum, cerebrospinal fluid, urine, or saliva, with plasma being the most preferred.

As used herein, "derivatizing" means reacting two molecules to form a new molecule. For example, an amino acid may be derivatized by reacting the amino acid with a derivatizing agent to form a derivatized amino acid. Derivatizing may include reacting the alpha amino group of the amino acid with an electrophilic atom of a derivatizing agent to form a covalent bond. Derivatizing agents may include isothiocyanate groups, dinitro-fluorophenyl groups, nitrophenoxycarbonyl groups, and/or phthalaldehyde groups.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationery phases and the bulk fluid, (i.e., mobile phase), as this fluid moves countercurrent to the stationary phases. The process is used for analysis and separation of mixtures of two or more substances. "Liquid chromatography" includes reverse phase liquid chromatography (RPLC) and high pressure liquid chromatography (HPLC).

As used herein, "mass spectroscopic" analysis or "mass spectrometry" (MS analysis) means an analytical technique to identify unknown compounds including: (1) ionizing the compounds and potentially fractionating the compounds to form charged compounds; and (2) detecting the molecular weight of the charged compound and calculating a mass-to-charge ratio (m/z). The compound may be ionized and detected by any suitable means. A "mass spectrometer" includes means for ionizing compounds and detecting charged compounds.

As used herein, "electrospray ionization" means a technique used in mass spectrometry to ionize macromolecules and to overcome the propensity of macromolecules to fragment. In "electrospray ionization" a liquid is pushed through a very small charged metal capillary by a carrier gas. The liquid contains the substance which is to be studied, the analyte, as well as a large amount of solvent, which is usually much more volatile then the analyte. The charge contained in the capillary transfers to the liquid which charges the analyte molecule. As like charges repel, the liquid pushes itself out of the capillary and forms a mist or an aerosol of small droplets about 10 μm across, to increase the distance between the similarly charged molecules. A neutral carrier gas is used to evaporate the neutral solvent in the small droplets, this in turn brings the charged analyte molecules closer together. The proximity of the molecules becomes unstable, however, and as the similarly charges molecules come closer together, the droplets once again explode. This process repeats itself until the analyte is free of solvent and a lone ion is formed. The lone ion is transported to a mass analyzer.

As used herein, a "quadrupole analyzer" is a mass analyzer composed of quads (i.e., two pairs of metallic rods aligned in parallel), wherein one pair of rods is at a positive electrical potential and the other set of rods is at a negative potential. To be detected, an ion must pass through the center of a trajectory path bordered and parallel to the aligned rods. When the quads are operated at a given amplitude of direct current and radio frequency voltages, only ions of a given m/z ratio will resonate and have a stable trajectory to pass through the quadrupole and be detected. "Positive ion mode" means a mode wherein positively charged ions are detected by the mass analyzer. "Negative ion mode" means a mode wherein negatively charged ions are detected by the mass analyzer. For "single ion monitoring" or "selected ion monitoring" (i.e., SIM), the amplitude of the direct current and the radio frequency voltages are set to observe only a specific mass.

As used herein, a "low molecular weight fraction" is a fraction that is enriched in one or more low molecular weight molecules. A low molecular weight molecule typically has a molecular weight of less than about 1000 daltons, and more typically less than about 500 daltons.

As used herein, "hydrophobic" means not dissolving or dissolving poorly in water. "Hydrophobic" compounds include long chain alkanes. A hydrophobic solvent is a solvent that is capable of dissolving a hydrophobic compound.

As used herein "about" when used in the context of a number means the number plus or minus 10%.

Disclosed is a method for identifying and/or quantifying amino acids in a body fluid. The body fluid can be blood, plasma, serum, bile, saliva, urine, cerebrospinal fluid, and the like. A preferred body fluids are plasma, serum, CSF, urine, or saliva, with plasma being the most preferred.

A set of individual amino acid standards representing the types of amino acids that might be present in a particular body fluid is preferably added to the body fluid sample before any processing. The set of amino acid standards preferably contains a known amount of each individual amino acid present in the set. A set of amino acid standards may include one or more amino acids from the group consisting of lysine, asparagine, threonine, serine, isoleucine, methionine, proline, histidine, glutamine, arginine, glycine, aspartic acid, glutamic acid, alanine, valine, phenylalanine, leucine, tyrosine, cysteine, tryptophan, phosphoserine, sulfo-cysteine, arginosuccinic acid, hydroxyproline, phosphoethanolamine, sarcosine, taurine, carnosine, citrulline, anserine, 1,3-methyl-histidine, alpha-amino-adipic acid, beta-alanine, ethanolamine, gamma-amino-butyric acid, beta-amino-isobutyric acid, alpha-amino-butyric acid, L-allo-cystathionine (cystathionine-A), L-cystathionine (cystathionine-B), cystine, allo-isoleucine, leucine, DL-hydroxylysine (hydroxylysine (1)), DL-allo-hydroxylysine (hydroxylysine (2)), ornithine, tryptophan, homocystine, and isomers thereof (e.g., stereoisomers).

The amino acids of the set of amino acid standards may be modified so that they can be easily discriminated from the corresponding amino acids found in the body fluid. The internal standard amino acid preferably behaves closest to the amino acid that it is chosen to represent chemically and physically but fragments to ions of a different mass upon mass spectrometric analysis. Thus, a preferred set of amino acids standards is deuterated.

Body fluid may be processed prior to derivatization to obtain an enriched preparation of the amino acids. Various procedures may be used for this purpose depending on the type of body fluid. These include filtration, precipitation, centrifugation, combinations thereof and the like. Separation of a low molecular weight fraction is a preferred approach. Size separation on small volumes of sample is preferably performed by filtering using a low molecular weight cutoff filter. The filtered body fluid sample (i.e., permeate) will include free amino acids and the retained components (i.e., retentate) will include high molecular weight components such as proteins. Suitable filters for generating a filtrate include 45 micron, 22 micron and 100,000, 50,000 and 10,000 dalton cutoff filters. In addition, high molecular weight components may be precipitated from the plasma sample by adding alcohol (e.g., methanol) or acid to the sample. High molecular weight components may also be removed from the sample by high speed centrifugation.

Derivatization of amino acids is performed following any necessary processing of the body fluid sample. The amino acids in the sample typically are derivatized to facilitate separation and/or detection of free amino acids in the sample during LC-MS (e.g., pre-column derivatization is first performed where LC is subsequently performed). The derivatizing agent may include substituents that facilitate detection of the derivatized amino acids during or after chromatography (e.g., fluorophores or chromophores). In addition, the derivatizing agent may include substituents that facilitate ionization of the derivatized amino acids during mass spectrometry. Typical derivatizing agents include isothiocyanates (e.g., phenyl isothiocyanate (PITC)), o-phthaldialdehyde (OPA), 2,4-dinitrofluorobenzene (DNFB), and Nα-(2, 4-dinitro-5-fluorophenyl)-L-alainamide (FDAA). In a preferred embodiment, the derivatizing agent is PITC.

After the amino acids in the sample have been derivatized, the sample is subjected to chromatographic separation, preferably high pressure liquid chromatographic separation, and mass spectrometry (i.e., LC-MS).

Liquid chromatography and mass spectrometry may be performed by placing the derivatized sample in an instrument that includes a chromatographic column in flow communication with a mass spectrometer. The chromatographic column typically includes a medium (i.e., a packing material) to facilitate separation of the derivatized amino acids (i.e., fractionation). The medium may include minute particles that have a diameter of approximately 2-6 μm, preferably about 3 μm. For example, the particles may be silica particles. The particles may have pores that have a diameter of approximately 50-300 angstroms, preferably 150 angstroms. Additionally, the particles may have a surface area of approximately 50-600 $m^2/g$, preferably 100 $m^2/g$.

The particles include a bonded surface that interacts with the derivatized amino acids to facilitate separation of the amino acids. One suitable bonded surface is a hydrophobic bonded surface such as an alkyl bonded surface. Alkyl bonded surfaces may include C-4, C-8, or C-18 bonded alkyl groups, preferably C-18 bonded groups.

The column may have any suitable dimensions. In particular, the column may have a diameter of about 0.5-5 mm and a length of about 15-300 mm. Preferably, the column has a diameter of about 2 mm and length of about 50 mm.

Suitable media for preparing a chromatographic column and/or prepared columns may be obtained from commercial sources. In particular, suitable columns may be obtained from Thermo Electron Corporation (e.g., 250×2.1 mm, 5 μm, BetaBasic C18 column).

The chromatographic column includes an inlet port for receiving a sample and an outlet port for discharging an effluent that includes the fractionated sample. In the method, the derivatized sample is applied to the column at the inlet port, eluted with a solvent or solvent mixture, and discharged at the outlet port. Different solvent modes may be selected for eluting the amino acids. For example, liquid chromatography may be performed using a gradient mode, an isocratic mode, or a polytyptic (i.e. mixed) mode. Preferably, liquid chromatography is performed using a gradient mode. In the gradient mode, the derivatized sample is applied to the column and a mixture of two solvents (i.e., the mobile phase) is passed through the column to elute the amino acids. Generally, as known in the art, one of the solvents will tend to be relatively hydrophilic, and the other solvent will tend to be relatively hydrophobic. As a specific example of a solvent combination found to be suitable in the practice of the present method, the hydrophilic solvent may be 95% $H_2O$, 5% acetonitrile and the hydrophobic solvent may be 100% acetonitrile. Optionally, the solvent combination may include one or more reagents to facilitate separation and/or detection of the derivatized amino acids (e.g., 20 mM ammonium acetate). Some reagents may be added to the mobile phase to improve the shape of the chromatographic peak and/or to provide a source of ions for LC-MS.

In most cases, to perform liquid chromatography with a gradient solvent, two pumps are used that mix the two solvents. Initially, as the solvents are mixed, the solvent mixture that is passed through the column (i.e., mobile phase) includes mostly hydrophilic solvent. Gradually, the amount of hydrophilic solvent in the mixture is decreased and the amount of hydrophobic solvent in the mixture is increased to create a solvent gradient. Ultimately, the solvent mixture that is passed through the column includes mostly hydrophobic solvent. In this manner, hydrophilic amino acids will be eluted before hydrophobic amino acids.

The mass spectrometer includes an inlet port for receiving the fractionated sample that is in flow communication with the outlet port of the chromatographic column. The mass spectrometer is capable of generating one or more mass spectroscopic data sets for identifying one or more amino acids in the sample. Suitable instruments for performing LC-MS may be obtained from commercial sources. In particular, suitable instruments for performing LC-MS may be obtained from Agilent Technologies (e.g., Agilent 1100 Series LC/MSD).

The mass spectrometer will include an ion source for ionizing the fractionated sample and creating charged molecules for further analysis. Ionization of the sample may be performed by electrospray ionization (ESI), atmospheric pressure chemical ionization (ACPI), photoinonization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. Electrospray ionization is preferred.

After the sample has been ionized, the positively charged or negatively charged ions thereby created may be analyzed to determine a mass-to-charge ratio (i.e., m/z). Preferably, the negatively charged ions are analyzed. Suitable analyzers for determining mass-to-charge ratios include quadropole analyzers, ion traps analyzers, and time-of-flight analyzers. Preferably, the mass-to-charge ratio is determined using a quadropole analyzer. The ions may be detected by using several detection modes. For example, selected ions may be detected (i.e., using a selective ion monitoring mode (SIM)), or alternatively, ions may be detected using a scanning mode. Preferably, the ions are detected by using SIM.

Example 1—Analytical Procedures

Urine, plasma, and cerebrospinal fluid (CSF) samples were obtained from normal individuals. Heparinized plasma samples were collected from patients after an overnight fast. Non-fasting samples for pediatric patients were used. The following procedure was used for amino acid quantification in urine, plasma, and CSF.

Deuterated internal standards were added to about 100 µl of the test material (i.e., plasma, urine, or CSF) to form a test mixture. The test mixture then was passed through a 10,000 molecular weight filter to provide a low molecular weight filtrate fraction as a test sample and then dried under nitrogen at 40-75° C. The dried sample was dissolved in about 25 µl of a redry solution (equal volumes of methanol, 1M sodium acetate, and triethylamine) and dried under nitrogen at 40° C. The sample was dissolved in 50 µl of a derivatizing solution (1.12 µl of 100% methanol, 1.60 µl water, 1.60 µl of 100% triethylamine, and 1.60 µl of 100 phenylisothiocyanate (PITC)). The dissolved sample was then heated at about 40° C. for about 15-20 minutes and then dried under liquid nitrogen at 50-60° C. The dried sample was dissolved in 100 µl of a reconstitution solution (95% $H_2O$, 5% acetonitrile), vortexed, and transferred to vials for LC/MS.

LC/MS determination of the sample amino acids was performed using an Agilent 1100 Series LC/MSD with a Thermo Beta-Basic C-18 (250×2.1 mm) HPLC column. The mobile phase consisted of (A) 20 mM ammonium acetate and (B) 100% acetonitrile, heated to 50° C. Sample amino acids were eluted from the column using a step-gradient as follows:

| Step | Time (minutes) | Mobile Phase % B | Flow (mL/Minute) | Maximum Pressure (bar) |
|---|---|---|---|---|
| 1 | 0.00 | 97.0 | 0.550 | 350 |
| 2 | 1.40 | 97.0 | 0.550 | 350 |
| 3 | 4.50 | 92.0 | 0.550 | 350 |
| 4 | 6.50 | 90.0 | 0.550 | 350 |
| 5 | 10.50 | 82.0 | 0.550 | 350 |
| 6 | 13.50 | 80.0 | 0.650 | 350 |
| 7 | 16.50 | 73.0 | 0.650 | 350 |
| 8 | 17.50 | 55.0 | 0.650 | 350 |
| 9 | 18.50 | 50.0 | 0.650 | 350 |
| 10 | 19.70 | 20.0 | 0.550 | 350 |
| 11 | 20.70 | 20.0 | 0.550 | 350 |
| 12 | 21.00 | 97.0 | 0.550 | 350 |

As the separated amino acids exit the HPLC column, they were introduced into the spray chamber where the effluent is sprayed and de-solvated by the electrospray ion source. The PITC derivatives were negatively charged during the electrospray process and then further separated through the quadrupole mass filter. Amino acid ions were detected and their abundances measured. The ratio of the area abundances of each amino acid ion to its internal standard was plotted against a six-point calibration curve. FIGS. 1 and 2 show the results of a typical run.

Example 2—Quantification of Amino Acid Content in Plasma

Amino acid analysis was performed on heparinized plasma samples obtained from neonates (≤30 days), infants (1-23.9 months), children (2-17.9 years), and adults (≥18 years). All individuals were assessed as clinically normal or obtained from samples submitted for infectious disease determinations. All subjects were fully ambulatory, community dwelling, healthy, and on no medications. The demographics of the test groups is as follows:

| Test Group | # of subjects (n) | # of males | # of females |
|---|---|---|---|
| Neonates (≤30 days) | 55 | 33 | 22 |
| Infants (1-23.9 months) | 115 | 59 | 56 |
| Children (2-17.9 years) | 134 | 76 | 58 |
| Adults (≥18 years) | 134 | 64 | 70 |

Based on the analysis of these plasma samples, normal Reference Ranges were constructed using standard parametric and non-parametric statistical procedures. If the data was determined to be Gaussian, the appropriate mean±2 SD range was chosen. If the data was non-gaussian, the non-parametric 95 percentile range or observed range was chosen. Table 1 provides normal reference ranges for each amino acid assayed, along with the limit of quantification (LOQ). Reference ranges are provided in µM (micromoles per liter). The normal range for amino acids which are undetectable should be taken to be less than or equal to the LOQ.

TABLE 1

Adult and Pediatric Amino Acid Levels in Plasma

| Amino Acid | LOQ | Neonates | Infants | Children | Adults |
|---|---|---|---|---|---|
| Pserine | N/A | ≤0.67 | ≤0.56 | Undetectable | ≤0.90 |
| Aspartic Acid | 1.0 | 2.4-19.5 | 2.3-14.3 | 1.3-8.2 | 0.9-3.9 |
| Sulfo-Cysteine | UNK | 0.13-1.60 | ≤1.66 | ≤1.62 | 0.44-3.95 |
| Glutamic Acid | 1.0 | 51-277 | 32-185 | 9-109 | 10-97 |
| Arginosuccinic Acid (ASA) | 1.0 | ≤1.15 | ≤1.10 | ≤1.00 | ≤1.00 |
| Hydroxyproline (OH-Proline) | 1.0 | 13-72 | 7-63 | 6-32 | 4-27 |
| Hawkinsin | 1.0 | Undetectable | Undetectable | Undetectable | Undetectable |
| Serine | UNK | 87-241 | 83-212 | 85-185 | 65-138 |
| Asparagine | 1.0 | 12-70 | 20-77 | 23-70 | 31-64 |
| α-Amino Adipic Acid (AAD) | 1.0 | ≤2.8 | ≤3.6 | ≤2.1 | ≤2.4 |
| Glycine | 4.0 | 133-409 | 103-386 | 138-349 | 122-322 |
| Glutamine | UNK | 240-1194 | 303-1459 | 405-923 | 428-747 |
| Sarcosine | 1.0 | ≤4.5 | ≤4.0 | ≤3.9 | ≤3.7 |
| Phospho-Ethanolamine (PEA) | 2.0 | Undetectable | Undetectable | Undetectable | Undetectable |
| β-Alanine (BALA) | 2.0 | ≤8.3 | ≤7.8 | ≤4.7 | ≤4.8 |
| Taurine | UNK | 29-161 | 26-130 | 32-114 | 31-102 |
| Histidine | UNK | 40-143 | 42-125 | 54-113 | 60-109 |
| Citrulline | 1.0 | 3-35 | 4-50 | 9-52 | 16-51 |
| Carnosine | 1.0 | ≤10.0 | ≤6.1 | Undetectable | Undetectable |
| Arginine | UNK | 14-135 | 30-147 | 38-122 | 43-407 |
| Threonine | UNK | 56-392 | 40-428 | 59-195 | 67-198 |
| Alanine | UNK | 83-447 | 119-523 | 157-481 | 200-483 |
| 1-Methylhistidine (1-Me-His) | 1.0 | ≤4.2 | ≤8.6 | ≤27.4 | ≤47.1 |
| Anserine | 1.0 | Undetectable | Undetectable | Undetectable | Undetectable |
| γ-Amino-Butyric Acid (GABA) | 1.0 | Undetectable | Undetectable | ≤2.2 | ≤3.1 |
| 3-Methylhistidine (3-Me-His) | 1.0 | ≤9.9 | ≤8.2 | 1.4-6.3 | 2.1-8.6 |
| β-Amino-Isobutyric Acid (BAIB) | 3.0 | ≤9 | ≤8 | ≤6 | Undetectable |
| Proline | 1.0 | 87-375 | 104-348 | 99-351 | 104-383 |
| Ethanolamine | UNK | 8-106 | 5-19 | 5-15 | 5-13 |
| α-Amino-Butyric Acid (AAB) | 1.0 | 1-20 | 4-30 | 6-30 | 7-32 |
| Cysteine | 1.0 | ≤5.3 | ≤16.3 | ≤34.6 | 6.6-73.5 |
| Tyrosine | UNK | 33-160 | 24-125 | 31-108 | 38-96 |
| Valine | UNK | 57-250 | 84-354 | 130-307 | 132-313 |
| Methionine | 1.0 | 13-45 | 12-50 | 14-37 | 16-34 |
| Cystathionine-A (Cysta-A) | 1.0 | Undetectable | Undetectable | Undetectable | Undetectable |
| Cystathionine-B (Cysta-B) | 1.0 | Undetectable | Undetectable | Undetectable | Undetectable |
| Cystine | 1.0 | ≤25 | ≤19 | ≤39 | 8-52 |
| Isoleucine | 1.0 | 12-92 | 10-109 | 33-97 | 34-98 |
| Allo-Isoleucine (allo-Ile) | UNK | Undetectable | Undetectable | Undetectable | Undetectable |
| Leucine | UNK | 23-172 | 43-181 | 65-179 | 73-182 |
| Hydroxy-Lysine-1 (OH-Lysine-1) | 1.0 | 3-10 | 1-8 | 1-4 | 1-7 |
| Hydroxy-Lysine-2 (OH-Lysine-2) | 1.0 | Undetectable | Undetectable | Undetectable | 2.34 or less |

TABLE 1-continued

Adult and Pediatric Amino Acid Levels in Plasma

| Amino Acid | LOQ | Neonates | Infants | Children | Adults |
|---|---|---|---|---|---|
| Homocystine | 1.0 | Undetectable | Undetectable | Undetectable | Undetectable |
| Phenylalanine | UNK | 30-79 | 31-92 | 38-86 | 40-74 |
| Tryptophan | 1.0 | 17-85 | 16-92 | 30-94 | 40-91 |
| Ornithine | 2.0 | 29-168 | 19-139 | 33-103 | 27-83 |
| Lysine | UNK | 66-226 | 70-258 | 98-231 | 119-233 |

Example 3—Quantification of Amino Acid Content in Urine

Amino acid analysis was performed on urine samples obtained from neonates (≤30 days), infants (1-23.9 months), children (2-17 years), and adults (>17 years). All individuals were assessed as clinically normal or obtained from samples submitted for infectious disease determinations. All subjects were fully ambulatory, community dwelling, healthy, and on no medications. The demographics of the test groups is as follows:

| Test Group | # of subjects (n) | # of males | # of females |
|---|---|---|---|
| Neonates (≤30 days) | 17 | 14 | 3 |
| Infants (1-23.9 months) | 40 | 23 | 17 |
| Children (2-17 years) | 80 | 42 | 38 |
| Adults (>17 years) | 111 | 55 | 56 |

The amino acid content of urine is initially measured on a concentration (μmol amino acid per liter of urine; μM) basis. The amino acid concentrations were then normalized based on the urinary creatinine levels and normal Reference Ranges were constructed using standard parametric and non-parametric statistical procedures. If the data was determined to be Gaussian, the appropriate mean±2 SD range was chosen. If the data was non-gaussian, the non-parametric 95 percentile range or observed range was chosen. Table 2 provides normal reference ranges (mmol/mol creatinine) for each amino acid assayed. The limit of quantification (LOQ) is based on the amino acid determination in urine, unadjusted for creatinine. The normal range for amino acids which are undetectable should be taken to be less than or equal to the LOQ.

TABLE 2

Adult and Pediatric Amino Acid Levels in Urine (mmol/mol creatinine)

| Amino Acid | LOQ (μM) | Neonates | Infants | Children | Adults |
|---|---|---|---|---|---|
| Pserine | 1 | ≤8 | ≤3 | Undetectable | ≤247 |
| Aspartic Acid | 1 | ≤7 | ≤11 | ≤2 | ≤2 |
| Sulfo-Cysteine | 1 | ≤50 | ≤45 | ≤30 | ≤11 |
| Glutamic Acid | 1 | 4-19 | 3-30 | ≤10 | ≤3 |
| Arginosuccinic Acid (ASA) | 1 | ≤15 | ≤9 | ≤6 | ≤4 |
| Hydroxyproline (OH-Proline) | 1 | 30-485 | 2-345 | ≤4 | ≤2 |
| Hawkinsin | 1 | Undetectable | Undetectable | Undetectable | Undetectable |
| Serine | 1 | 44-454 | 39-422 | 13-127 | 10-71 |
| Asparagine | 1 | 8-42 | 5-132 | 3-42 | 2-37 |
| α-Amino Adipic Acid (AAD) | UNK | ≤10 | ≤36 | ≤34 | ≤11 |
| Glycine | 1 | 215-2053 | 105-413 | 23-413 | ≤330 |
| Glutamine | UNK | ≤355 | 41-396 | 18-188 | 21-182 |
| Sarcosine | 1 | ≤18 | ≤19 | ≤2 | ≤69 |
| Phospho-Ethanolamine (PEA) | 2 | ≤23 | ≤32 | ≤15 | ≤4 |
| β-Alanine (BALA) | 2 | ≤9 | ≤15 | ≤5 | ≤10 |
| Taurine | 1 | ≤650 | ≤670 | ≤255 | ≤232 |
| Histidine | 1 | 40-301 | 56-543 | 9-425 | 17-266 |
| Citrulline | 1 | ≤4 | ≤13 | ≤4 | ≤2 |
| Carnosine | 1 | 9-72 | 15-65 | ≤23 | ≤8 |
| Arginine | 2 | ≤30 | ≤35 | ≤8 | ≤5 |
| Threonine | 1 | ≤112 | 9-158 | 4-60 | 4-46 |
| Alanine | UNK | 45-264 | 16-294 | 8-156 | 9-67 |
| 1-Methylhistidine (1-Me-His) | 1 | ≤16 | 4-71 | 5-400 | ≤204 |

TABLE 2-continued

Adult and Pediatric Amino Acid Levels in Urine (mmol/mol creatinine)

| Amino Acid | LOQ (µM) | Neonates | Infants | Children | Adults |
|---|---|---|---|---|---|
| Anserine | 1 | ≤8 | ≤30 | ≤87 | ≤411 |
| γ-Amino-Butyric Acid (GABA) | 1 | ≤1.4 | ≤1.5 | ≤1.6 | ≤1.6 |
| 3-Methylhistidine (3-Me-His) | UNK | 9-45 | 14-35 | 11-40 | 10-35 |
| β-Amino-Isobutyric Acid (BAIB) | 3 | ≤269 | ≤309 | ≤133 | ≤88 |
| Proline | 1 | ≤219 | ≤216 | ≤11 | ≤2 |
| Ethanolamine | 1 | 87-490 | 54-176 | 27-114 | 21-65 |
| α-Amino-Butyric Acid (AAB) | 1 | ≤7 | ≤7 | ≤5 | ≤2 |
| Cysteine | 1 | Undetectable | Undetectable | ≤4 | ≤5 |
| Tyrosine | UNK | 4-59 | 10-69 | 3-48 | 3-19 |
| Valine | 2 | 2-20 | 4-21 | 2-20 | 2-5 |
| Methionine | 1 | ≤7 | ≤7 | ≤5 | ≤2 |
| Cystathionine-A (Cysta-A) | 1 | ≤2 | ≤1 | ≤2 | ≤3 |
| Cystathionine-B (Cysta-B) | 1 | ≤20 | ≤29 | ≤8 | ≤5 |
| Cystine | UNK | 15-58 | 6-28 | 3-20 | 3-13 |
| Isoleucine | 3 | ≤9 | ≤12 | ≤5 | ≤3 |
| Allo-Isoleucine (allo-Ile) | 1 | Undetectable | Undetectable | Undetectable | Undetectable |
| Leucine | 2 | ≤23 | ≤24 | ≤13 | ≤6 |
| Hydroxy-Lysine-1 (OH-Lysine-1) | 1 | ≤83 | ≤71 | ≤8 | ≤8 |
| Hydroxy-Lysine-2 (OH-Lysine-2) | 1 | ≤3 | ≤3 | Undetectable | Undetectable |
| Homocystine | 1 | Undetectable | ≤4 | Undetectable | Undetectable |
| Phenylalanine | UNK | 3-24 | 6-39 | 2-22 | 2-9 |
| Tryptophan | 1 | 2-21 | 5-46 | 2-27 | 2-14 |
| Ornithine | 2 | ≤39 | ≤11 | ≤5 | ≤4 |
| Lysine | UNK | 13-284 | 4-239 | 3-112 | 3-59 |
| Hydroxy-Lysine, Total | 1 | 5-117 | 2-72 | ≤8 | ≤8 |
| Cystathionine, Total | 1 | 2-20 | ≤29 | ≤8 | ≤9 |

Example 4—Quantification of Amino Acid Content in Cerebrospinal Fluid (CSF)

Amino acid analysis was performed on CSF samples obtained from neonates (≤3 months), infants (3-23.9 months), children (2-10 years), and adults (>10 years). All individuals were assessed as clinically normal or obtained from samples submitted for infectious disease determinations. All subjects were fully ambulatory, community dwelling, healthy, and on no medications. The demographics of the test groups is as follows:

| Test Group | # of subjects (n) | # of males | # of females |
|---|---|---|---|
| Neonates (≤3 months) | 27 | 23 | 4 |
| Infants (3-23.9 months) | 22 | 16 | 6 |
| Children (2-10 years) | 21 | 9 | 12 |
| Adults (>10 years) | 57 | 21 | 36 |

Based on the analysis of these CSF samples, normal Reference Ranges were constructed using standard parametric and non-parametric statistical procedures. If the data was determined to be Gaussian, the appropriate mean±2 SD range was chosen. If the data was non-gaussian, the non-parametric 95 percentile range or observed range was chosen. Table 3 provides normal reference ranges for each amino acid assayed, along with the limit of quantification (LOQ). Reference ranges are provided in µM (micromoles per liter). The normal range for amino acids which are undetectable should be taken to be less than or equal to the LOQ.

TABLE 3

Adult and Pediatric Amino Acid Levels in CSF

| Amino Acid | LOQ | Neonates | Infants | Children | Adults |
|---|---|---|---|---|---|
| Pserine | N/A | ≤4.62 | ≤2.39 | ≤3.85 | ≤4.19 |
| Aspartic Acid | 1.0 | ≤2.7 | Undetectable | Undetectable | ≤2.0 |
| Sulfo-Cysteine | UNK | 0-1 | 0-1 | 0-1 | 0-1 |
| Glutamic Acid | 1.0 | 1-9 | ≤5.1 | ≤10.6 | 1.1-13.2 |
| Arginosuccinic Acid (ASA) | 1.0 | ≤4.3 | ≤2.4 | ≤3.0 | ≤2.5 |
| Hydroxyproline (OH-Proline) | 1.0 | 0.9-3.9 | ≤1.6 | Undetectable | ≤1.7 |
| Hawkinsin | 1.0 | Undetectable | Undetectable | Undetectable | Undetectable |
| Serine |  | 30-88 | 22-61 | 15-62 | 9-41 |
| Asparagine | 1.0 | ≤27 | ≤13 | ≤25 | ≤24 |
| α-Amino Adipic Acid (AAD) | 1.0 | Undetectable | Undetectable | Undetectable | Undetectable |
| Glycine | 4.0 | 3-26 | ≤12 | ≤13 | ≤10 |
| Glutamine | UNK | 525-1583 | 386-742 | 377-1738 | 361-1175 |
| Sarcosine | 1.0 | Undetectable | Undetectable | Undetectable | Undetectable |
| Phospho-Ethanolamine (PEA) | 2.0 | Undetectable | Undetectable | ≤4.2 | ≤4.8 |
| β-Alanine (BALA) | 2.0 | Undetectable | Undetectable | Undetectable | Undetectable |
| Taurine | UNK | 0-18 | ≤8 | 1-8 | 1-8 |
| Histidine | UNK | 8-32 | 4-25 | 7-25 | 7-22 |
| Citrulline | 1.0 | 1-4 | ≤3 | 1-2 | ≤2 |
| Carnosine | 1.0 | Undetectable | Undetectable | Undetectable | Undetectable |
| Arginine | UNK | 2-27 | 7-32 | 9-31 | 10-32 |
| Threonine | UNK | 23-104 | 10-55 | 8-85 | 12-64 |
| Alanine | UNK | 13-50 | 8-48 | 5-62 | 1-107 |
| 1-Methylhistidine (1-Me-His) | 1.0 | ≤6.4 | ≤9.0 | ≤3.8 | ≤4.2 |
| Anserine | 1.0 | ≤26 | ≤27 | ≤19 | ≤28 |
| γ-Amino-Butyric Acid (GABA) | 1.0 | Undetectable | Undetectable | ≤2.2 | ≤3.1 |
| 3-Methylhistidine (3-Me-His) | 1.0 | ≤3.3 | ≤1.8 | ≤2.5 | ≤2.7 |
| β-Amino-Isobutyric Acid (BAIB) | 3.0 | Undetectable | Undetectable | Undetectable | Undetectable |
| Proline | 1.0 | ≤3.9 | ≤2.3 | ≤1.7 | ≤5.9 |
| Ethanolamine | UNK | 1-46 | 3-19 | 5-40 | 4-23 |
| α-Amino-Butyric Acid (AAB) | 1.0 | ≤6 | ≤6 | 1-11 | 1-11 |
| Cysteine | 1.0 | Undetectable | Undetectable | Undetectable | Undetectable |
| Tyrosine | UNK | 9-41 | 5-20 | 5-32 | 5-18 |
| Valine | UNK | 11-31 | 8-19 | 2-37 | 7-42 |
| Methionine | 1.0 | 2-14 | 1-7 | ≤9 | 1-8 |
| Cystathionine-A (Cysta-A) | 1.0 | Undetectable | Undetectable | Undetectable | Undetectable |
| Cystathionine-B (Cysta-B) | 1.0 | Undetectable | Undetectable | Undetectable | Undetectable |
| Cystine | 1.0 | ≤3.7 | ≤3.2 | ≤1.6 | ≤2.2 |
| Isoleucine | 1.0 | 3-11 | 3-7 | 2-13 | 3-10 |
| Allo-Isoleucine (allo-Ile) | UNK | Undetectable | Undetectable | Undetectable | Undetectable |
| Leucine | UNK | 7-22 | 7-12 | 8-27 | 9-32 |
| Hydroxy-Lysine-1 (OH-Lysine-1) | 1.0 | Undetectable | Undetectable | Undetectable | Undetectable |
| Hydroxy-Lysine-2 (OH-Lysine-2) | 1.0 | Undetectable | Undetectable | Undetectable | Undetectable |
| Homocystine | 1.0 | Undetectable | Undetectable | ≤2.5 | ≤2.1 |
| Phenylalanine | UNK | 4-31 | 4-14 | ≤2.5 | 6-31 |
| Tryptophan | 1.0 | ≤5.9 | ≤7.7 | 0.6-4.6 | ≤9.3 |
| Ornithine | 2.0 | ≤25.7 | ≤4.5 | ≤4.7 | ≤14.2 |
| Lysine | UNK | 6-38 | 3-29 | 9-58 | 19-60 |

Example 5—Quantification of Amino Acid Content in Saliva

Amino acid analysis was performed on saliva samples of nine (9) adults (3 males and 6 females). All individuals were assessed as clinically normal and were fully ambulatory, community dwelling, healthy, and on no medications. Table 4 provides the actual measured ranges of amino acid levels. For diagnostic purposes, these ranges may be considered "normal" ranges. The normal range for amino acids which are undetectable should be taken to be less than or equal to the LOQ.

TABLE 4

Adult Amino Acid Levels in Saliva

| Amino Acid | Normal Range |
|---|---|
| Aspartic Acid | 2.6-9.2 |
| Arginosuccinic Acid (ASA) | Undetectable |
| Sulfo-Cysteine | ≤1.3 |
| Glutamic Acid | 1.5-26.0 |
| Hydroxyproline (OH-Proline) | ≤1.6 |
| Serine | 0.9-4.9 |
| Asparagine | Undetectable |
| Phospho-Ethanolamine (PEA) | ≤133.8 |
| α-Amino Adipic Acid (AAD) | 0.4-2.8 |
| Glycine | 24.5-425.9 |
| Glutamine | 0.7-20.2 |
| Sarcosine | 0.4-11.0 |
| Histidine | 4.3-59.8 |
| β-Alanine (BALA) | ≤6.0 |
| Taurine | 26.5-177.5 |
| Citrulline | 1.5-21.7 |
| Carnosine | 0.0 |
| Threonine | 0.1-0.4 |
| Arginine | 4.9-26.4 |
| Anserine | ≤0.1 |
| 1-Methylhistidine (1-Me-His) | ≤0.8 |
| 3-Methylhistidine (3-Me-His) | ≤0.4 |
| Alanine | 7.6-39.6 |
| γ-Amino-Butyric Acid (GABA) | 0.4-2.4 |
| β-Amino-Isobutyric Acid (BAIB) | ≤1.0 |
| Proline | 10.5-264.1 |
| Ethanolamine | 5.1-42.3 |
| α-Amino-Butyric Acid (AAB) | ≤0.6 |
| Tyrosine | 8.5-63.1 |
| Valine | 0.3-7.9 |
| Methionine | 0.4-0.9 |
| Cystathionine-A (Cysta-A) | Undetectable |
| Cystathionine-B (Cysta-B) | Undetectable |
| Cystine | ≤3.7 |
| Isoleucine | 0.4-1.7 |
| Allo-Isoleucine (allo-Ile) | Undetectable |
| Leucine | 0.2-6.1 |
| Hydroxy-Lysine-1 (OH-Lysine-1) | ≤0.1 |
| Hydroxy-Lysine-2 (OH-Lysine-2) | Undetectable |
| Homocystine | Undetectable |
| Phenylalanine | 3.8-31.5 |
| Tryptophan | ≤1.2 |
| Ornithine | 4.8-72.0 |
| Lysine | 6.2-81.0 |

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses which will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

Thus, additional embodiments are within the scope of the invention and within the following claims.

What is claimed is:

1. A method for determining the amount of at least two amino acids in a cerebrospinal fluid (CSF) sample by tandem mass spectrometry, the method comprising:
    (a) purifying the at least two amino acids comprising taurine and beta alanine by liquid chromatography (LC); and
    (b) ionizing the at least two amino acids under conditions suitable to produce ions detectable by mass spectrometry;
    (c) detecting the amount of ions of the at least two amino acids by tandem mass spectrometry (MS/MS);
    (d) determining the amount of the at least two amino acids in the sample from the amount of ions determined in step (c).

2. The method of claim 1, wherein the at least two amino acids further comprise cystine and lysine.

3. The method of claim 1, wherein the at least two amino acids further comprise aspartic acid, threonine, serine, asparagine, glutamic acid, glutamine, glycine, alanine, citrulline, valine, cystine, methionine, isoleucine, leucine, tyrosine, phenylalanine, gamma-amino-butyric acid, lysine, and histidine.

4. The method of claim 1, wherein the at least two amino acids further comprise aspartic acid, hydroxyproline, threonine, serine, asparagine, glutamic acid, glutamine, sarcosine, alpha-amino-adipic acid, proline, glycine, alanine, alpha-amino-butyric acid, valine, cysteine, methionine, homocitrulline, cystathionine, alloisoleucine, isoleucine, leucine, tyrosine, phenylalanine, arginosuccinic acid, beta amino-isobutyric acid, homocystine, gamma-amino-butyric acid, tryptophan, hydroxylysine, lysine, and histidine.

5. The method of claim 1, wherein the amount of the two or more amino acids is used to diagnose or monitor one or more diseases selected from the group consisting of Maple Syrup Urine Disease, kidney failure, Crohn's disease, ulcerative colitis, chronic fatigue syndrome, Wilson's disease, Cushing's disease, gout, and hyperactivity disorders.

6. The method of claim 1, wherein the method comprises using one or more internal standards.

* * * * *